US00PP20392P2

(12) United States Plant Patent
Pieters

(10) Patent No.: US PP20,392 P2
(45) Date of Patent: Oct. 6, 2009

(54) ***CHRYSANTHEMUM* PLANT NAMED 'PPP COL RD07'**

(50) Latin Name: *Chrysanthemum morifolium*
Varietal Denomination: PPP COL RD07

(75) Inventor: Dirk Pieters, Oostnieuwkerke (BE)

(73) Assignee: Paraty BVBA, Oostnieuwkerke (BE)

( * ) Notice: Subject to any disclaimer, the term of this patent is extended or adjusted under 35 U.S.C. 154(b) by 0 days.

(21) Appl. No.: 12/218,835

(22) Filed: Jul. 18, 2008

(51) Int. Cl.
*A01H 5/00* (2006.01)

(52) U.S. Cl. ..... Plt./293

(58) Field of Classification Search ..... Plt./293
See application file for complete search history.

*Primary Examiner*—June Hwu
(74) *Attorney, Agent, or Firm*—Mark P. Bourgeois

(57) ABSTRACT

A new and distinct *Chrysanthemum* plant cultivar is disclosed, characterized by small decorative type inflorescences, consistent flowering response to short days, blooming consistently after 49 days of short day length, dark red ray florets, free branching habit, and a consistent natural season flowering habit during the second week of September.

1 Drawing Sheet

Latin name of the genus and species: *Chrysanthemum morifolium.*

Variety denomination: 'PPP COL RD07 '.

BACKGROUND OF THE INVENTION

The new cultivar 'PPP COL RD07' is a product of a naturally occurring whole plant mutation of 'PPP COL OR07' (U.S. Plant patent application Ser. No. 12/218,798). The new cultivar was discovered in an indoor greenhouse and selected by Dirk Pieters in September of 2003 in Oostnieuwkerke, Belgium.

Asexual reproduction of the new cultivar 'PPP COL RD07' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP COL RD07' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP COL RD07.' These characteristics in combination distinguish 'PPP COL RD07' as a new and distinct *Chrysanthemum* cultivar:

1. Small, dark red, decorative-type inflorescences;
2. Consistent natural season flowering habit during the second week of September;
3. Free branching habit; and
4. Consistent flowering response to short days, blooming consistently after 49 days of short day length.

Plants of the new cultivar 'PPP COL RD07' are similar to plants of the parent variety, 'PPP COL OR07' in most horticultural characteristics, however plants of the new cultivar 'PPP COL RD07' are taller and wider. Also, the new cultivar 'PPP COL RD07' has more inflorescences per lateral branch.

Finally, 'PPP COL RD07' has red ray florets compared to the bronze-orange ray florets of the parent 'PPP COL OR07.'

In comparison to the commercially available variety 'GEDI TWO CAM' (U.S. Plant Pat. No. 14,472), 'PPP COL RD07' is slightly taller and has a wider plant spread. Additionally, the new variety 'PPP COL RD07' has a natural blooming season one week later than the comparable variety as well as longer inflorescence longevity. Further, the new variety 'PPP COL RD07' has more inflorescences per lateral branch, more ray florets per inflorescence and has a smaller inflorescence diameter. Finally, the ray florets of the new variety 'PPP COL RD07' have a distinct yellow base that is not present on the florets of 'GEDI TWO CAM'.

BRIEF DESCRIPTION OF THE PHOTOGRAPH

The accompanying photograph illustrates in full color a typical plant of 'PPP COL RD07' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP COL RD07' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* 'PPP COL RD07.'

Commercial classification: Garden-type *Chrysanthemum*.

PROPAGATION

Time to rooting: 7 to 14 days at approximately 21° C.

Root description: Fine, fibrous.

PLANT

Growth habit: Mounding herbaceous perennial.
Height: Approximately 20.5 cm.
Plant spread: Approximately 39 cm.
Growth rate: Moderate.
Branching characteristics: Free branching.
Length of lateral branches: Approximately 14 cm.
Number of leaves per lateral branch: Approximately 28.
Age of plant described: Approximately 140 days.

FOLIAGE

Leaf:
*Arrangement.*—Alternate single.
*Average length.*—Approximately 3.3 cm.
*Average width.*—Approximately 1.7 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 1 cm.
*Color.*—Young foliage upper side: Near Yellow-Green 147A. Young foliage under side: Near Yellow-Green 147B. Mature foliage upper side: Near Yellow-Green 147A. Mature foliage under side: Near Green 137A.
*Venation.*—Type: Palmately net. Venation color upper side: Near Green 138C. Venation color under side: Near Green 138C.
Petiole:
*Average length.*—Approximately 1 cm.
*Color.*—Near Green 138C.
*Diameter.*—Approximately 0.2 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately the second week in September.
*Number of inflorescences per lateral branch.*—Approximately 18.
*Inflorescence diameter.*—Approximately 3.8 cm.
*Inflorescence depth.*—Approximately 1 cm.
*Inflorescence longevity on plant.*—Approximately 28 to 31 days.
*Persistence.*—Persistent.
Ray florets:
*Appearance.*—Matte.
*Texture.*—Smooth.
*Average number of ray florets per inflorescence.*—176.
*Shape.*—Oblanceolate.
*Aspect.*—Flat.
*Margin.*—Entire.
*Apex.*—Obtuse.
*Length.*—Approximately 1.1 cm.
*Width.*—Approximately 0.7 cm.
*Color.*—Upper surface at first opening: Slightly darker than Red 46A. Upper surface at maturity: Near Red 46A and near Yellow 9A at very base. Upper surface at fading: Near Greyed-Red 178B with shades of near Yellow 9A rising up in longitudinal lines from the base. Under surface at first opening: Near Red 46A. Under surface at maturity: Near Red 46A with shades of near Yellow 9A rising up in longitudinal lines from the base. Under surface at fading: Near Greyed-Red 178D with more pronounced lines longitudinal lines of near Yellow 8A rising up from the base.
Disc florets:
*Appearance.*—Shiny.
*Texture.*—Smooth.
*Average number of florets per disc.*—Approximately 2.
*Shape.*—Cylindric.
*Apex.*—Obtuse.
*Average length.*—Approximately 0.2 cm.
*Average width.*—Approximately 0.1 cm.
*Color.*—At first opening: Near Yellow-Green 154A. At maturity: Near Yellow 13A. At fading: Near Yellow 13A.
Peduncle:
*Length.*—At terminal end (shortest): Approximately 5.2 cm. At lateral end (longest): Approximately 4 cm.
*Angle to stem.*—Acute.
*Strength.*—Moderate.
*Color.*—Near Green 138B.
*Habit.*—Upright.
*Diameter.*—Approximately 0.2 cm.
*Surface texture.*—Lightly pubescent.
Inflorescence bud:
*Length.*—Approximately 0.4 cm.
*Diameter.*—Approximately 0.6 cm.
*Form.*—Globular.
*Color.*—Near Yellow-Green 154D.
Involucral bracts (phyllaries):
*Appearance.*—Matte.
*Texture.*—Lightly pubescent.
*Number.*—Approximately 28.
*Shape.*—Ovate.
*Margin.*—Entire.
*Apex.*—Acute.
*Length.*—Approximately 0.5 cm.
*Width.*—Approximately 0.2 cm.
*Color.*—Upper side: Near Green 137A. Under side: Near Green 137B.

REPRODUCTIVE ORGANS

Ray florets:
*Number of pistils per floret.*—1.
*Stigma shape.*—2 branched.
*Stigma color.*—Near Yellow 9A.
*Style color.*—Near Green-Yellow 1D.
*Style length.*—Approximately 0.3 cm.
*Stamens.*—Absent.
Disc florets:
*Number of pistils per floret.*—1.
*Stigma shape.*—Cylindric.
*Stigma color.*—Near Yellow 2A.
*Style length.*—Approximately 0.2 cm.
*Style color.*—Near Yellow-Green 154C.
*Number of stamens per floret.*—Approximately 5.
*Anther shape.*—Tubular.
*Anther color.*—Near Yellow 2A.
*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP COL RD07' as herein illustrated and described.

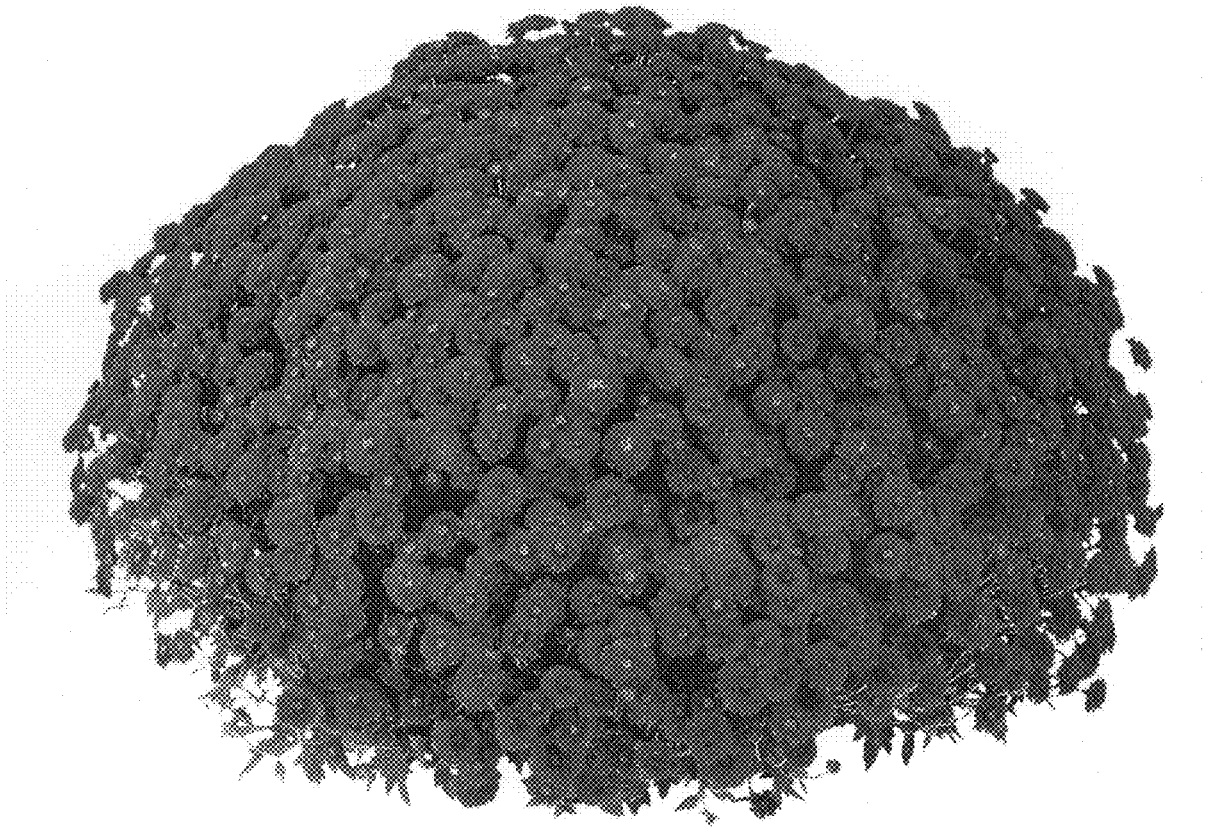

* * * * *